(12) United States Patent
Grey et al.

(10) Patent No.: US 6,272,383 B1
(45) Date of Patent: Aug. 7, 2001

(54) ELECTRO-ACUPUNCTURE METHOD USING AN ELECTRICAL STIMULATOR

(75) Inventors: Thomas L. Grey; Gregory J. Gruzdowich, both of Carlsbad, CA (US)

(73) Assignee: Woodside Biomedical, Inc., Carlsbad, CA (US)

(*) Notice: Subject to any disclaimer, the term of this patent is extended or adjusted under 35 U.S.C. 154(b) by 0 days.

(21) Appl. No.: 09/345,609

(22) Filed: Jun. 28, 1999

(51) Int. Cl.[7] ............................... A61N 1/18; A61N 1/32
(52) U.S. Cl. .................. 607/72; 607/63; 128/907
(58) Field of Search .................. 607/72, 2, 63, 607/33, 32, 115; 128/907

(56) References Cited

U.S. PATENT DOCUMENTS

| | | | |
|---|---|---|---|
| 4,664,118 | * 5/1987 | Batters | 128/421 |
| 4,981,146 | 1/1991 | Bertolucci | 128/802 |
| 5,950,635 | * 9/1999 | Garcia-Rill et al. | 128/898 |
| 5,957,951 | * 9/1999 | Cazaux et al. | 606/204 |
| 6,002,965 | * 12/1999 | Katz et al. | 607/48 |
| 6,152,140 | * 11/2000 | Blum | 128/898 |

FOREIGN PATENT DOCUMENTS

3609536-C1 * 3/1987 (DE) .............. A61N/1/04

* cited by examiner

*Primary Examiner*—Carl Layno
(74) *Attorney, Agent, or Firm*—K. David Crockett, Esq.; Crockett & Crockett

(57) ABSTRACT

A method of reducing nausea, dizziness, stomach pain and other symptoms in a patient utilizing a non-invasive nerve stimulation device applied over acupuncture points and nerves in the ankle or calf of the patient.

4 Claims, 2 Drawing Sheets

ELECTRO-ACUPUNCTURE METHOD USING AN ELECTRICAL STIMULATOR

FIELD OF THE INVENTIONS

This invention relates to moderation of nausea and electro-acupuncture.

BACKGROUND OF THE INVENTIONS

Bertolucci, Nausea Control Device, U.S. Pat. No. 4,981,146, Jan. 1, 1991, describes a nausea control device in the form of a watch-like housing attachable to the human wrist by an adjustable attachment band. The device uses non-invasive nerve stimulation whereby electricity is passed through two electrodes to stimulate nerves located on the inside of the wrist. The treatment provided by the device is sometimes referred to as electro-acupuncture, which is a form of acupuncture, and the ventral site of application is referred to in the acupuncture art as the P6 point, pericardium 6 point, or master point of the pericardium meridian (sometimes referred to as the vascular meridian). A primary object of the invention is to provide a non-chemical, non-invasive, painless and inexpensive method of alleviating nausea. It is also portable, self-contained and convenient to the patient. Electrical pulse repetition rate of approximately 70 pulses per second and a pulse width of 80 microseconds has been found to provide effective relief of nausea in a patient. Our currently preferred electrical pulse pattern comprises about 350 microsecond pulse width at about 31 pulses per second at power levels of about 10–35 milli-amps peak pulse height. Thus a wide range of pulse patterns may be used in non-invasive nerve stimulation devices.

SUMMARY

The methods and devices described below use electro-acupuncture applied to acupuncture points on the calf and around the ankle to control nausea, stomach upset and similar conditions. A patient desiring to moderate his or her nausea places a pair of electrodes on the ankle, lower calf or upper calf, and applies electrical stimulation to the ankle through these electrodes. This has the effect of reducing nausea and stomach upset. The electrodes, pulse generating circuitry, and power supply are most conveniently packaged in a housing which is held to the ankle, lower calf or upper calf with a band. The device is placed so that the electrodes overlie an acupuncture point known to affect a desired therapy. Alternatively, the device is placed so that the electrodes overlie a nerve that runs under the acupuncture point, in which case the device may be placed on the leg some distance from the associated acupuncture point to provide a comfortable placement for the device. The technique accomplished by the device is referred to as electro-acupuncture or non-invasive nerve stimulation.

DETAILED DESCRIPTION OF THE INVENTIONS

Figure 1:
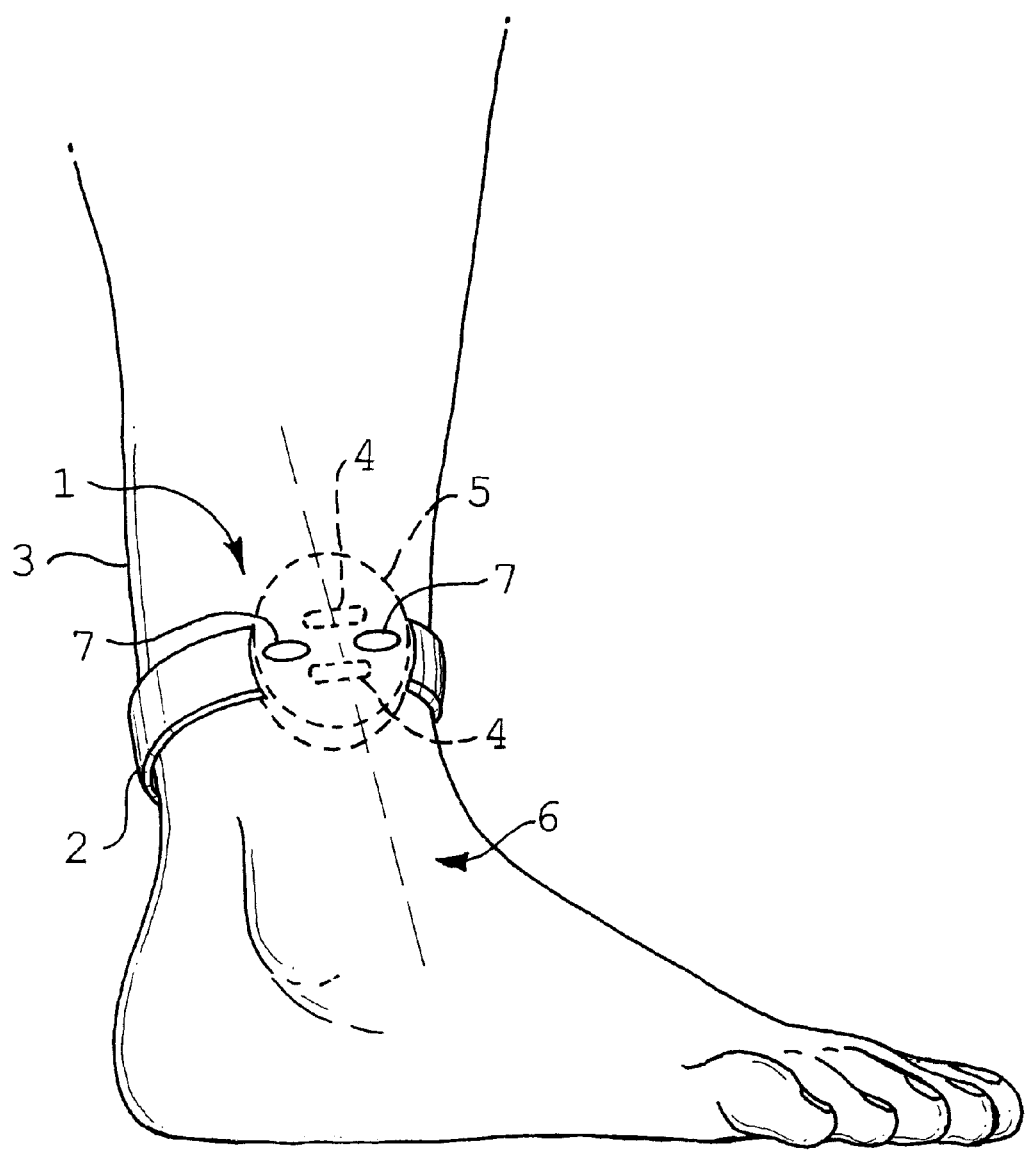
FIG. 1 illustrates the non-invasive nerve stimulation suitable for use on the ankle and lower leg.

FIG. 1 illustrates the non-invasive nerve stimulation suitable for use on the ankle and lower leg. The ReliefBand® NST™ non-invasive nerve stimulation device 1 was secured with strap 2 which is sized for applying the device to the calf 3 or ankle of a patient. The pair of electrodes 4 are disposed on the underside of the housing 5 so that they lie over the nerve 6 which is to be stimulated by the device (indicated by the phantom line). The electrodes are thus located in spaced side-by-side relation along the line of the nerve or over the acupuncture point targeted for stimulation. Control buttons 7 are mounted on the outer surface of the device, and permit the user to adjust the power of stimulation and the pulse pattern of stimulation. The strap is used to hold the electrodes in contact with the skin in the vicinity of the target nerve or acupuncture point. The required battery and control electronics are housed within the housing, and input mechanisms are located on the outer face of the housing.

Figure 2:
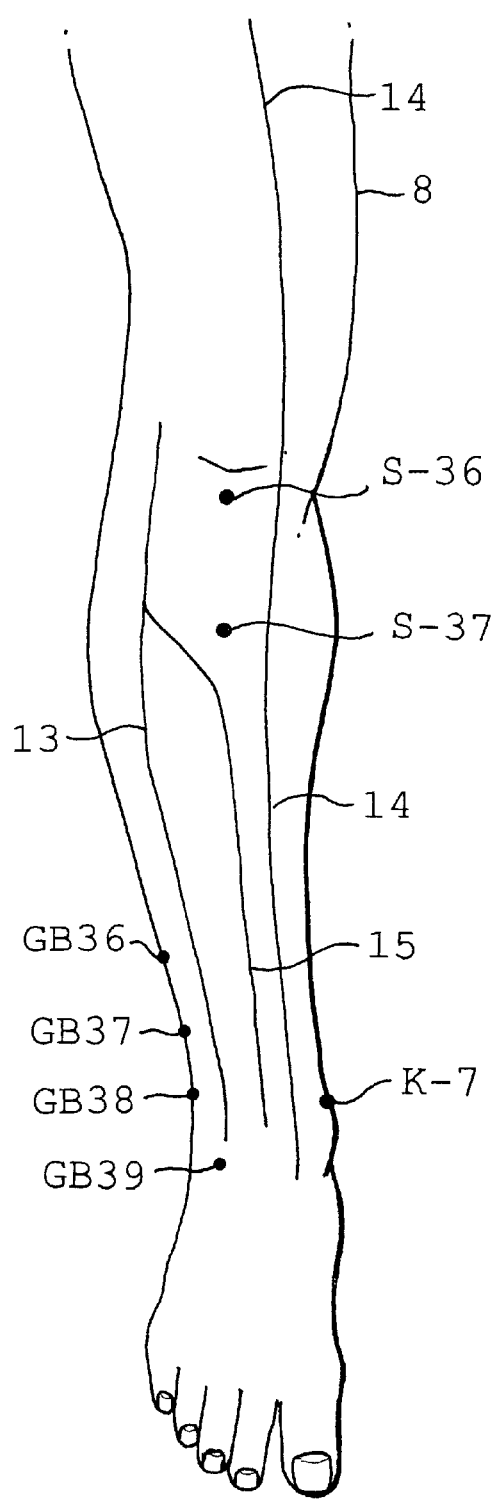
FIG. 2 shows the acupuncture points of the leg, in an anterior view.

The target nerve or target acupuncture point is found on the ankle or leg of the patient. The anterior view of the leg 8 is shown in FIG. 2, which also shows several useful acupuncture points for application of electro-stimulation. The S-36 point (or zu san li) (also referred to as ST-36) is located just below the knee cap, slightly lateral to the anterior crest of the tibia. The S-37 (shang ju xu)(also referred to as ST-37) point is located several inches below the knee cap, slightly lateral to the anterior crest of the tibia. These points can be stimulated to relieve nausea and vomiting. The GB-39 (xuan zhong) point is located about 3 inches above the external malleolus, on the lateral side of the calf. Acupuncture points GB-38, GB-37 and GB 36 are also locates along a line extending up along the lateral side of the calf, above GB-39. The K-7 (fu liu) point is located on the medial side of the calf, posterior to the medial malleolus, toward the achilles tendon. The GB-39 GB-38, GB-37 and GB 36 and KI-7 points may be stimulated to relieve diarrhea and intestinal problems.

Figure 3:
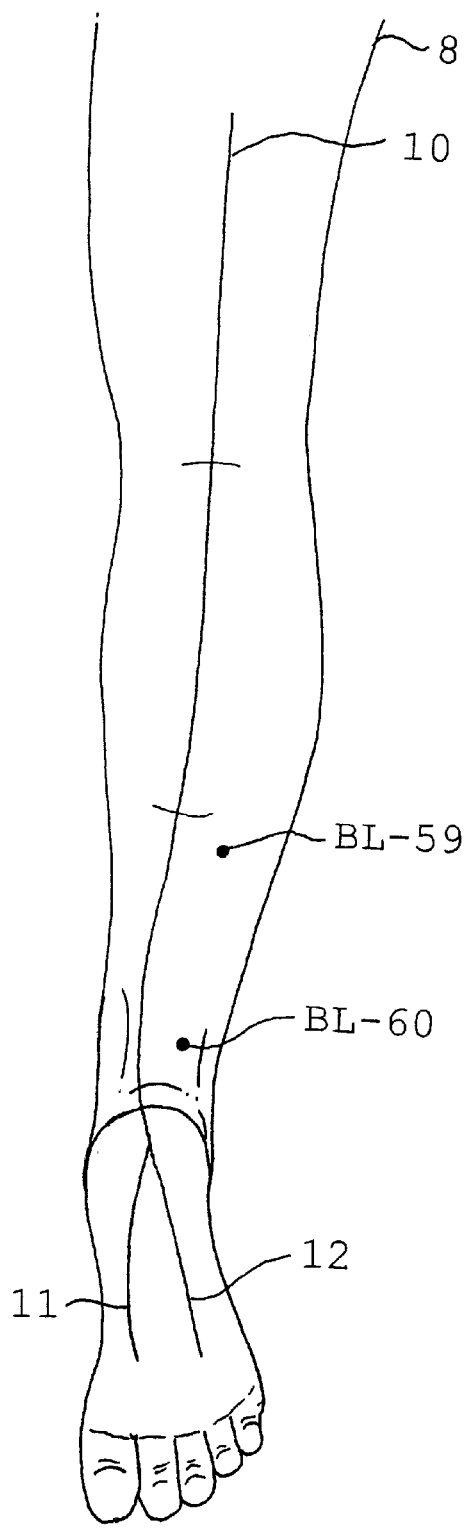
FIG. 3 shows the acupuncture points of the leg, in a posterior view.

The posterior view of the leg 8 is shown in FIG. 3, which also shows several useful acupuncture points for application of electro-stimulation. The BL-60 point (or kun lun) is located just lateral to the achilles tendon, between the posterior border of the external malleolus and the medial aspect of the tendo calcaneous. The BL-59 point (or fu yang) is located just posterior to the external malleolus. These points may be stimulated to reduce symptoms such as nausea, dizziness and motion sickness.

Thus, all of these acupuncture points may be stimulated by the application of non-invasive electrical stimulation to achieve the desired therapy of relief from stomach pain and vomiting, dizziness, motion sickness, abdominal pain, diarrhea and pre-menstrual cramps.

Referring to the local anatomy of the ankle, several nerves are associated with channels of acupuncture points (the "channel" including all the acupuncture points having the same two letter designation or other traditional groupings), and can be stimulated to provide therapeutic relief. Along the back of the calf and ankle, the tibial nerve 10 and its branches (e.g., the medial plantar nerve 11 and lateral plantar nerves 12 under the foot, generally traveling inside the ankle) and elements of the musculo-cutaneous nerve and its branches (generally traveling outside the ankle) can be stimulated to cause the same affect as stimulation of the traditional SP and BL acupuncture points. The tibial nerve and its branches run along the path established by the BL and SP acupuncture points. This indicates that, for the SP-2, SP-3 and SP-4 (Spleen Channel) acupuncture points, and the BL-55, BL-59, and BL-60 acupuncture points, their associated nerve structures can be stimulated by electrodes at the back of the ankle, since this is a convenient location for placement of a bracelet or wristwatch-like, wearable battery powered device. The nerve stimulation device can also be placed strapped onto the calf just below the knee, with the electrodes on the back of the need, in contact with the crease of the joint, to contact the BL points and the tibial nerve in its superficial approach to the skin in this area. These SP and BL points are all associated with relieving stomach pain, nausea, vomiting, dizziness, motion sickness, abdominal pain, diarrhea and pre-menstrual cramps. Other possible sites around the foot are generally implicated in relieving menstrual and pre-menstrual symptoms in women. Thus, stomach pain, nausea, vomiting, dizziness, motion sickness, abdominal pain, diarrhea and pre-menstrual cramps may be alleviated by application of electrical stimulation to the tibial nerve and its branches wherever it can be accessed.

Referring to the anterior view of FIG. 2, the superficial peroneal nerve 13 runs along the outside of the calf, along the line established by the GB points. Thus, the superficial peroneal nerve may be stimulated with the device to cause the affects associated with the GB channel of acupuncture points. These points are associated with relieving stomach pain and vomiting, dizziness, motion sickness, abdominal pain, diarrhea and pre-menstrual cramps. The saphenous nerve 14 lies along the K channel which included point K7, and may be stimulated with the nerve stimulation device at superficial points along its path, for example near the inside of the upper calf, just below the knee, or at the bottom of the calf, but well above the ankle bone. The deep peroneal nerve 15 runs down the front of the calve, along the line defined by the S-36 and S-37 points, and may be stimulated with the nerve stimulation device at superficial points along its path.

Generally, the points near the ankle represent points accessible to acupuncture needles where certain nerves run superficially (close to the skin). Because the electro-acupuncture device does not require penetration, but is capable of deeper stimulating penetration than needles due to its application of non-invasive electrical stimulation, the sites of stimulation may be altered from the traditional acupuncture points. Thus, rather than placing the device immediately above the acupuncture points on the bony part of the ankle (or points requiring that the band be strapped over the ankle bone), the stimulation may be applied at alternate sites well above the ankle, so long as the stimulation is applied to the nerve associated with the acupuncture channel associated with the acupuncture point which is traditionally targeted for the desired therapy.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of controlling nausea in a patient comprising the steps of:

mounting a pair of electrodes onto the calf of the patient at a position generally closely overlying the GB-39 acupuncture point, wherein said electrodes are carried in a housing with a band adapted to be fastened about the calf, with the housing having a pulsed stimulation signal generating circuit and a portable power supply encased therein;

generating a pulsed stimulation signal of selected amplitude, pulse width and cycle rate; and delivering the stimulation signal to the electrodes to stimulate the ankle generally at the GB-39 acupuncture point to suppress nausea.

2. The method of claim 1 further including the step of adjustably varying the amplitude of the stimulation signal.

3. A method of controlling nausea in a patient comprising the steps of:

mounting a pair of electrodes onto the calf of the patient at a position generally closely overlying the S-37 acupuncture point, wherein the electrodes are carried in a housing with a band adapted to be fastened about the calf just below the knee, with the housing having a pulsed stimulation signal generating circuit and a portable power supply encased therein;

generating a pulsed stimulation signal of selected amplitude, pulse width and cycle rate; and delivering the stimulation signal to the electrodes to stimulate the calf generally at the S-36 acupuncture point to suppress nausea.

4. The method of claim 3 further including the step of adjustably varying the amplitude of the stimulation signal.

* * * * *

UNITED STATES PATENT AND TRADEMARK OFFICE
CERTIFICATE OF CORRECTION

PATENT NO. : 6,272,383 B1 Page 1 of 1
DATED : August 7, 2001
INVENTOR(S) : Thomas L. Grey et al.

It is certified that error appears in the above-identified patent and that said Letters Patent is hereby corrected as shown below:

Column 4,
Line 30, "S-37 point" should read -- S-36 point --.

Signed and Sealed this

Sixteenth Day of July, 2002

Attest:

Attesting Officer

JAMES E. ROGAN
Director of the United States Patent and Trademark Office